United States Patent
Seidman

(10) Patent No.: US 6,416,479 B1
(45) Date of Patent: Jul. 9, 2002

(54) METHOD FOR USING BREATH CARBON MONOXIDE CONCENTRATION MEASUREMENTS TO DETECT PREGNANT WOMEN AT RISK FOR OR EXPERIENCING VARIOUS PATHOLOGICAL CONDITIONS RELATING TO PREGNANCY

(75) Inventor: Daniel Seidman, Tel-Hashomer (IL)

(73) Assignee: Natus Medical, Inc., San Carlos, CA (US)

( * ) Notice: Subject to any disclaimer, the term of this patent is extended or adjusted under 35 U.S.C. 154(b) by 67 days.

(21) Appl. No.: 09/616,536

(22) Filed: Jul. 14, 2000

(51) Int. Cl.[7] ............................................... A61B 5/08

(52) U.S. Cl. .................... 600/532; 600/529; 600/543

(58) Field of Search ............................. 600/529, 531, 600/532, 533, 534, 538, 535, 536, 537, 539, 540, 541, 542, 543

(56) References Cited

U.S. PATENT DOCUMENTS

| | | | | | |
|---|---|---|---|---|---|
| 5,293,875 | A | * | 3/1994 | Stone | 600/532 |
| 5,361,771 | A | * | 11/1994 | Craine et al. | 600/532 |
| 5,383,469 | A | * | 1/1995 | Vreman et al. | 600/532 |
| 5,404,885 | A | * | 4/1995 | Sheehan et al. | 600/529 |
| 5,826,577 | A | * | 10/1998 | Perroz, Jr. et al. | 600/532 |

OTHER PUBLICATIONS

Sibai BM. Hypertension in Pregnancy. In: Gabbe SG, Niebyl JR, Simpson JL (eds.). Obstetrics: Normal & Problem Pregnancies. New York, Churchill Livingstone, 1996.

Isler CM, Rinehart BK, Terrone DA, Martin RW, Magann EF, Martin JN Jr., Maternal mortality associated with HELLP (hemolysis, elevated liver enzymes, and low platelets) syndrome. Am J Obstet Gynecol 1999; 181:924–8.

Padden MO. HELLP syndrome: recognition and perinatal management. Am Fam Physician 1999;60:829–36.

Dotsch J, Hohmann M, Kuhl PG. Neonatal morbidity and mortality associated with maternal haemolysis elevated liver enzymes and low platelets syndrome. Eur. J Pediatr 1997;156:389–91.

Lu GC, Goldenberg RL. Current concepts on the pathogenesis and markers of preterm births. Clin Perinatol 2000 Jun.;27(2):263–83.

Pharmacol Res 1998 May; 37:403–8.

Acevedo and Ahmed, Hemeoxygenase 1– inhibits human myometrial contractility via carbon monoxide and is upregulated by progesterone during pregancy J. Clin. Invest. 1998 Mar.; 101: 949–55.

Barber A, Robson SC, Lyall F, Hemoxygenase abd Nitric Oxide Synthase do not maintain human uterine quiescence during preganancy. Am. J. Pathol. 1999;5:831–840.

Kreiser et al., The role of heme oxygenase (HO) in regulation of somatic growth factors in pregnancy.

Yachie A, Niida Y, Wada T, Igarashi N, Kaneda H, Toma T, et al. Oxidative stress causes enhanced endothelial cell injury in human heme oxygenase–1 deficiency. J Clin Invest 1999;103(1):129–35.

Abraham NG, Lin JH, Mitrione SM, Schwartzman ML, Levere RD, Shibahara S. Expression of heme oxygenase gene in rat and human liver. Biochem Biophys Res Commun 1988;150(2):717–22.

Rodgers PA, Lee CS, Stevenson DK, Dennery PA. Ontogeny of lung heme oxygenase in the neonatal Wistar rat. Pediatr Res 1995.

Fiona L, Barber A, Myatt L, Bulmer JN, Robson SC. Hemoeoxygenase expression in human placenta and placental bed implies a role in regulation of trophoblast invasion and placental function. The FASEB Journal. 2000;14:208–219.

Underwood PB, Kesler KF, O'Lane JM, Callagan DA. Parental smoking empirically related to pregnancy outcome. Obstet Gynecol 1976;29:1–8.

Duffus GM, MacGillivray I. The incidence of pre–eclamptic toxaemia in smokers and non–smokers. Lancet 1968;1:994–5.

Andres RL, Larrabee K. The perinatal consequences of smoking and alcohol use. Curr Probl Obstet Gynecol Fertil 1996;19:167–206.

Seidman DS, Mashiach S. Involuntary smoking and pregnancy. Eur J Obstet Gynecol Reprod Biol 1991;41:105–116.

(List continued on next page.)

*Primary Examiner*—Kevin Shaver
*Assistant Examiner*—Navin Natnithithadha
(74) *Attorney, Agent, or Firm*—Orrick, Herrington & Sutcliffe LLP

(57) ABSTRACT

A non-invasive method for the early detection and assessment of the severity of various pathological conditions in pregnancy including pregnancy-induced hypertension, preeclampsia, premature uterine contractions and intrauterine growth retardation. The carbon monoxide or end-tidal carbon monoxide concentration is measured in a pregnant woman's breath and compared to thresholds for determining the likelihood of onset or actual onset of these pathological conditions. The measurements can be made in a clinic, hospital, physician's office, or any other location easily accessible to pregnant women using any of a number of devices for measuring breath carbon monoxide. One solution is to measure end-tidal breath carbon monoxide using the Natus® CO-Stat® End Tidal Breath Analyzer, manufactured and sold by Natus Medical Inc. of San Carlos, Calif. This particular device allows an operator to perform non-invasive, simple and rapid, automatic sampling and analysis of end-tidal carbon monoxide in expiratory air without the requirement for laboratory analysis or highly trained personnel. Thus, the method can be employed using a device that does not required laboratory analysis or highly trained personnel, and results in an on-the-spot, immediate determination which is vital for rapid treatment of these serious conditions of pregnancy.

56 Claims, 16 Drawing Sheets

OTHER PUBLICATIONS

Ananth CV, Smulian JC, Vintzileos AM. Incidence of placental abruption in relation to cigarette smoking and hypertensive disorders during pregnancy: a meta–analysis of observational studies. Obstet Gynecol 1999;93:622–8.

Cnattingius S, Mills JL, Yuen J, Eriksson O, Salonen H. The paradoxical effect of smoking in preeclamptic pregnancies: smoking reduces the incidence but increases the rates of perinatal mortality, abrupt placentae, and intrauterine growth restriction. Am J Obstet Gynecol 1997;177:156–61.

Conde–Agudelo A, Althabe F, Belizan JM, Kafury–Goeta AC. Cigarette smoking during pregnancy and risk of preeclampsia: a systematic review. Am J Obstet Gynecol 1999;181:1026–35.

Lain KY, Powers RW, Krohn MA, Ness RB, Crombleholme WR, Roberts JM. Urinary cotinine concentration confirms the reduced risk of preeclampsia with tobacco exposure. Am J Obstet Gynecol 1999;181:1192–6.

Zhang J, Klebanoff MA, Levine RJ, Puri M, Moyer P. The puzzling association between smoking and hypertension during preganancy. Am J Obstet Gynecol 1999;181:1407–13.

Mattar F, Sibai BM. Prediction and prevention of preeclampsia. Seminars in Perinatology 1999;23:58–64.

Vedernikov YP, Graser T, Vanin AF. Similar endothelium–dependent arterial relaxation by carbon monoxide and nitric oxide. Biomed Biochim Acta 1989;48:601–3.

Graser T, Vedernikov YP, Li DS. Study on the mechanism of carbon monoxide induced endothelium–independent relaxation in porcine coronary artery and vein. Biomed Biochim Acta 1990;49:293–296.

Odrcich MJ, Graham CH, Kimura KA, McLaughlin BE, Marks GS, Nakatsu K, Brien JF. Heme oxygenase and nitric oxide synthase in the placenta of the guinea–pig during gestation. Placenta 1998;19:509–16.

Ramos KS, Lin H. McGrath J.J. Modulation of cyclic guanosine monophosphate levels in cultured aortic smooth muscle cells by carbon monoxide. Biochem Pharmacol. 1989;38:1368–1370.

Committee on Technical Bulletins of the American College of Obstetricians and Gynecologists. ACOG technical bulletin. Hypertension in pregnancy. No. 219. Int J Gynaecol Obstet 1996;53:175–83.

Vreman HJ, Baxter LM, Stone RT, Stevenson DK. Evaluation of a fully automated end–tidal carbon monoxide instrument for breath analysis. Clin Chem 1996;42:50–56.

Vreman HJ, Wong RJ, Harmatz P, Fanaroff AA, Berman B, Stevenson DK. Validation of the Natus CO–Stat™ end–tidal breath analyzer in children and adults. J Clin Monitor Comput 1999;15:421–7.

Seidman DS, Paz I, Merlet–Aharoni I, Vreman HJ, Stevenson DK, Gale R. Noninvasive validation of tobacco smoke exposure in late pregnancy using end–tidal carbon monoxide measurements. J Perinatol 1999;19:358–361.

Secker–Walker RH, Vacek PM, Flynn BS, Mead PB. Smoking in pregnancy exhaled carbon monoxide, and birth weight. Obstet Gynecol 1997;89:648–53.

Martasek P, Schwartzman ML, Goodman AI, Solangi KB, Levere RD, Abraham NG. Hemin and 1–arginine regulation of blood pressure in spontaneous hypertensive rats. J Am Soc Nephrol 1991;2:1078–1084.

Levere RD, Martasek P, Escalante B, Schwartzman ML, Abraham NG. Effect of heme arginate administration on blood pressure in spontaneously hypertensive rats. J. Clin. Invest. 1990:86:213–219.

Rodgers PA, Vreman HJ, Dennery PA, Stevenson DK. Sources of carbon monoxide in biological systems and applications of CO detection technologies. Seminar Peinatol 1994;18:2–10.

Rees DD, Palmer RMJ, Moncada S. Role of endothelium–derived nitric oxide in the regulation of blood pressure. Proc Natl Acad Sci USA 1989;86:3375–3378.

Morris NH, Sooranna SR, Learmont JG, Poston L, Ramsey B, Pearson JD, Steer PJ. Nitric oxide synthase activities in placental tissue from normotensive, pre–eclamptic and growth retarded pregnancies. Br J Obstet Gynaecology 1995;102:711–714.

Seligman SP, Buyon JP, Clancy RM, Young BK, Abramson SB. The role of nitric oxide in the pathogenesis of preeclampsia. Am J Obstet Gynecol 1994:171:944–948.

Brüne B, Ullrich V. Inhibition of platelte aggregation by carbon monoxide is mediated by activation of guanylate cyclase. Mol Pharmacol 1987;32:497–504.

Tsukimori K, Maeda H, Ishida K, Nagata H, Koyanagi T, Nakano H. The superoxide generation of neutrophils in normal and pre–eclamptic pregnancies. Obstet Gynecol 1993;81:536–540.

Hubel CA, Roberts JM, Taylor RN, Musci TJ, Rogers GM, McLaughlin MK. Lipid peroxidation in pregnancy: New perspectives on pre–eclampsia. Am J Obstet Gynecol 1989;161:1025–1034.

Roberts JM, Taylor RN, Goldfien A. Clinical and biochemical evidence of endothelial cell dysfunction in the pregnancy syndrome preeclampsia. Am J Hypertens 1991;4:700–708.

Seidman DS, Paz I, Merlet–Aharoni I, Vreman HJ, Stevenson DK, Gale R. Non invasive validation of tobacco smoke exposure in late pregnancy using end–tidal carbon monoxide measurements. J Perinatol 19:358–361, 1999.

Seidman DS, Hallak M, Kelly DK, Guidice L. Stevenson DK, Abromovici H, Dennery PA. The role of carbon monoxide (CO) in the pathogenesis of preeclampsia. Society of Perinatal Obstetricians. Anaheim, California, Jan. 24, 1997. Am J Obstet Gynecol. 176:S101, 1996.

Seidman DS, Stevenson KD, Kelly DK, Dennery PA. The role of the heme catabolic pathway in pregnancy. Western Society of Pediatric Research (WSPR) Carmel, California, Feb. 7, 1997. J Invest Med, 46:A, 1997.

Baum M, Schiff E, Kreiser D, Dennery PA, Stevenson DK, Rosenthal T, Seidman DS. The paradoxical protective effect of smoking and preeclampsia: is carbon monoxide the missing link? Annual of Meeting of Maternal Fetal Medicine. Miami, Florida, Jan. 24, 1999. Am J Obstet Gynecol 182:S86, 2000.

Baum M, Schiff E, Kreiser D, Dennery PA, Stevenson DK, Rosenthal T, Seidman DS. Carbon monoxide and pregnancy induced hypertension. Annual meeting of the Israel Society of Perinatology. Tel–Aviv, Israel, Jun. 1999. Isr J. Obstet Gyenecol 10:82, 1999.

Seidman DS, Hendler D, Baum M, Kreiser D, Schiff E, Stevenson DK, Dennery PA. Pregnant women with uterine contractions have lower end tidal carbon monoxide levels. The 1st HO/CO meeting. New York, New York, Jul. 2000. Acta Hematol 103 (Suppl) 62, 2000.

Seidman DS, Hallak M, Kelly DK, Guidice L, Stevenson DK, Abromovici H, Dennery PA. The role of carbon monoxide (CO) in the pathogenesis of preeclampsia. Western Society of Pediatric Research (WSPR). Carmel, California, Feb. 10, 1997. J Invest Med, 46:A, 1997.

McLean M, Bowman M, Clifton V, Smith R, Grossman AB. Expression of the heme oxygenase–carbon monoxide signalling system in human placenta. J Clin Endocrinol Metab. 2000 Jun.;85(6);2345–2349.

Dennery PA, Rodgers PA. Ontogeny and developmental regulation of heme oxygenase. Journal of perinatology. 16:2, 1996. 79–88.

Longo M, Jain V, Vedernikov Y, Saade GR, Goodrum L, Facchinetti F, Garfield R. Effect of nitric oxide and carbon monoxide on uterine contractility during human and rat pregnancy. University of Texas Medical Branch. 1999. 981–988.

Baum M, Schif E, Kreiser D, Dennery P, Stevenson D, Rosenthal T, Seidman D. End tidal carbon monoxide measurement in women with pregnancy induced hypertension and preeclampsia.

* cited by examiner

PIH/PET STUDY TEST DATA
ETCOc (ppm) by Study Group

|         | PIH/PET Group (n=52) | 1st Trimester Control Group (n=42) | 3rd Trimester Control Group (n=63) | Non-pregnant Control Group (n=46) |
|---------|----------------------|------------------------------------|------------------------------------|-----------------------------------|
| Mean ±SD | 1.29* ±0.35 | 1.72 ±0.46 | 1.77 ±0.48 | 1.72 ±0.54 |
| Median | 1.3 | 1.6 | 1.7 | 1.7 |
| Range | 0.7 - 2.3 | 1.3 - 4.0 | 1.7 - 3.2 | 1.0 - 3.1 |

PIH/PET STUDY TEST DATA
ETCOc (ppm) by Medical Center

| Mean ± SD | PIH/PET | 3rd Trimester Control |
|---|---|---|
| Stanford, CA (n=11/22) | 1.35 ± 0.23* | 1.80 ± 0.55 |
| Cleveland, OH (n=20/21) | 1.40 ± 0.34# | 1.65 ± 0.24 |
| Sheba, Israel (n=21/20) | 1.16 ± 0.10* | 1.70 ± 0.54 |

PIH/PET STUDY TEST DATA
ETCOc (ppm) by Study Group

| | PIH/PET Group (n=52) | 1st Trimester Control Group (n=42) | 3rd Trimester Control Group (n=63) | Non-pregnant Control Group (n=46) |
|---|---|---|---|---|
| ≤ 1.2 | 46.2%* | 0% | 11.1% | 15.2% |
| ≤ 1.4 | 69.2%* | 14.3% | 19.0% | 26.1% |
| ≤ 1.6 | 86.5%* | 52.4% | 46% | 47.8% |

PIH/PET STUDY TEST DATA
Study Groups Gestational Age

|            | PIH (n=52)      | Controls 3rd Trimester (n=63) |
|------------|-----------------|-------------------------------|
| Mean (w) ± SD | 33.76 ± 3.85 | 33.57 ± 3.83                  |
| Range (w)  | 26 - 41         | 27 - 40                       |

FIG. 5

PMC STUDY TEST DATA
Study Group Characteristics

|  | Study Group (n=23) | Control Group (n=32) |
|---|---|---|
| Maternal Age Mean ± SD (yr) | 28.5 ± 4.5 | 2.9 ± 4.0 |
| Gravidity, Median (range) | 2 (1-4) | 3 (1-5) |
| Parity Median (range) | 1 (0-2) | 1 (0-3) |

FIG. 8

PMC STUDY TEST DATA
Study Groups Gestational Age

|  | PMC (n=10) | Term Labor (n=13) | No Contr. At Term (n=32) |
|---|---|---|---|
| Mean ± SD (w) | 29.2* ± 3.0 | 39.8 ± 1.8 | 39.7 ± 1.6 |
| Range (w) | 13 - 34 | 33 - 42 | 34 - 41 |

PMC STUDY TEST DATA
ETCOc (ppm) by Study Group

|  | Study Group (n=23) | Control Group (n=32) |
|---|---|---|
| Mean ± SD | 1.08 ± 0.36 | 1.70 ± 0.52* |
| Median | 1.2 | 1.6 |
| Range | 0.3 - 1.6 | 0.7 - 3.2 |

PMC STUDY TEST DATA
ETCOc (ppm) by Study Group

|  | PMC (n=10) | Term Labor (n=13) |
|---|---|---|
| Mean ± SD | 0.99 ± 0.38 | 1.15 ± 0.41 |
| Median | 0.95 | 1.2 |
| Range | 0.3 - 1.5 | 0.4 - 1.6 |

FIG. 11

PMC STUDY TEST DATA
ETCOc (ppm) by Study Group

|  | PMC (n=10) | Term Labor (n=13) | Control Group (n=32) |
|---|---|---|---|
| Mean ± SD | 0.99 ± 0.38* | 1.15 ± 0.41* | 1.70 ± 0.52 |
| Median | 0.95 | 1.2 | 1.6 |
| Range | 0.3 - 1.5 | 0.4 - 1.6 | 0.7 - 3.2 |

PMC STUDY TEST DATA
ETCOc (ppm) by Study Group

| | Study Group (n=23) | Control Group (n=32) |
|---|---|---|
| < 1.2 | 11 (47.8%) | 3 (9.4%)# |
| < 1.3 | 15 (65.2%) | 5 (15.6%)* |
| < 1.6 | 22 (95.7%) | 12 (37.5%)* |

PMC STUDY TEST DATA
ETCOc (ppm) by Study Group

|  | PMC (n=10) | Term Labor (n=13) |
|---|---|---|
| < 1.2 | 7 (70.0%) | 4 (30.8%)# |
| < 1.3 | 7 (70.0%) | 8 (61.5%) |
| < 1.6 | 10 (100%) | 12 (92.3%) |

METHOD FOR USING BREATH CARBON MONOXIDE CONCENTRATION MEASUREMENTS TO DETECT PREGNANT WOMEN AT RISK FOR OR EXPERIENCING VARIOUS PATHOLOGICAL CONDITIONS RELATING TO PREGNANCY

FIELD OF THE INVENTION

The present invention relates generally to methods for using breath carbon monoxide ("CO"), more particularly end-tidal carbon monoxide ("ETCOc") concentration measurements, to predict the occurrence of various pathological conditions during pregnancy as well as methods for using such measurements to determine the actual onset of such conditions.

BACKGROUND OF THE INVENTION

A. Pregnancy Induced Hypertension, Preeclampsia and the HELLP Syndrome

Pregnancy-induced hypertension ("PIH") is a common medical complication of pregnancy which encompasses a group of disorders including preeclampsia ("PET"). PET is primarily a disease of the last trimester of pregnancy and is the most common medical complication of pregnancy. It has a reported incidence ranging between 5% and 10% depending on the population demographics.[1] As the pathogenesis of these disorders is unclear, prediction and prevention remain an elusive goal.

PET is more common in a woman's first pregnancy and in women whose mothers or sisters had PET. The risk is also higher in women carrying multiple babies, in teenagers, and in women older than 40. Other women at risk include those with high blood pressure or kidney disease before becoming pregnant. The exact cause of PET is unknown. Symptoms of PET often include high blood pressure and proteinuria, and, in severe cases, headaches, blurring of vision and seizures. PET is often referred to by care providers as the "great masquerader" given its ability to mimic many other conditions such as the flu, a kidney infection or gallbladder disease.

End-organ damage, especially to the kidneys and liver, may result if the condition is not recognized early enough, and the condition can be life-threatening. Consequences for the late-term fetus include diminished placental blood flow, and subsequent wasting and asymmetrical growth of the fetus. At present, the best cure for the disease is delivery of the preterm baby followed by intensive neonatal care for the baby and intensive surgical care for the mother.

No single test is currently known which can diagnose PET. A pregnant woman's blood pressure is generally checked at each doctor's visit and a surge in blood pressure can be an early sign of PET. A urine test can determine if protein has been excreted in the urine. Certain blood tests may also indicate PET. When signs of PET appear, a doctor should watch the pregnant woman closely, possibly even daily, for rises in blood pressure, swelling, or urine excretion.

PET, and especially its severe variant, the HELLP (Hemolysis, Elevated Liver Enzymes and Low Platelets) Syndrome, a syndrome with a reported incidence in PET of between 2% and 12%, are frequently misdiagnosed at initial presentation.[2] The pathogenesis of the HELLP Syndrome remains unclear. Hemolysis, defined as the presence of microangiopathic hemolytic anemia, is the hallmark of the HELLP Syndrome.[3] The diagnosis of hemolysis in pregnant women is currently based on an abnormal peripheral blood smear, increased bilirubin >1.2 mg/dl and an increased lactic dehydrogenase >600 IU/L.[4] However, it is difficult to identify women at risk for HELLP Syndrome as severe hypertension is not a constant or even a frequent finding in the HELLP Syndrome.[5] Early diagnosis is critical because the morbidity and mortality rates associated with the severe forms of this disease have been reported to be as high as 25 percent.[6] Neonatal morbidity and mortality are also high in these pregnancies.[7]

Since a delay in diagnosing PET can be fatal[8], a better means of identifying women destined to develop PET is desirable. An accurate predictive test may allow timely transfer of patients to centers where adequate intervention and treatment could be promptly provided. Thus far, no test exists that satisfies the criteria for a suitable screening.[9]

B. Premature Labor

Premature labor remains an important problem facing modern care-givers of pregnant women, demanding tremendous costs for the care of prematurely born infants. Preterm birth is the major cause of perinatal morbidity and mortality in the world. Prematurity is responsible for 75% of infant deaths and 50% of the long-term neurological handicaps, including cerebral palsy, blindness, deafness, and slow development. The survival rate of neonates is improved by 2% per day from the 23rd to the 26th week of pregnancy (i.e., from 16% at 23 weeks to 57% at 26 weeks), reaching an 80% survival rate at 28 weeks, and greater than 90% by 30 weeks of gestation. Therefore, any treatment that prevents or delays premature birth will profoundly reduce neonatal mortality and morbidity rates. However, the use of premature delivery depends on accurate early identification of premature uterine contractions ("PMC").[10]

Recent attention has focused on the part that NO might play in maintaining myometrial (uterine smooth muscle) quiescence during pregnancy. CO, like NO, stimulates soluble guanylyl cyclase, thereby raising intracellular levels of cGMP in smooth muscle to produce relaxation. It has been suggested that the L-arginine-NO system may contribute to uterine quiescence during gestation and the initiation of labor at term.[11]

CO may similarly suppress myometrial contractility. The expression of large increases during pregnancy of heme oxygenase ("HO"), which catalyzes the degradation of heme to biliverdin and CO, has recently been demonstrated in the human myometrium.[12] Furthermore, Acevedo and Ahmed have recently shown that induction of HO produces CO that limits uterine contractility in pregnant myometrium indicating a role for the HO—CO-cGMP pathway in the maintenance of the quiescent state of the uterus during pregnancy.[13] A subsequent study did not support an up-regulation of HO during pregnancy and the data was inconsistent with a major role for CO in human myometrial quiescence.[14]

It has recently been found in an analysis of heme oxygenase-1 ("HO-1") immunoreactive protein of rat uterus and placenta that, during pregnancy, the expression of HO increases, up to day 16, then decreases toward delivery.[15] Similarly, in rat tissues during pregnancy it has been found that in the myometrium and placenta, HO-1 mRNA levels increase during pregnancy, up to day 16, then decrease towards delivery.

C. Intrauterine Growth Retardation

Intrauterine growth retardation ("IUGR") is an important cause of perinatal morbidity and mortality. The pathophysiology that precedes the development of IUGR remains incompletely understood. The importance of the placental blood flow to the growing fetus is obvious. The possible role of HO and its by-product CO in the regulation of blood pressure and blood flow have only been realized over the last few years.

Recently, a case of heme oxygenase-1 ("HO-1") deficiency was presented.[16] The patient had a complete loss of exon-2 of the maternal allele and a two-nucleotide deletion within exon-3 of the paternal allele. This child had severe growth retardation, hemolytic anemia, low bilirubin levels, elevated thromomodulin and Von Wilebrand factor as well as iron deposition in the liver and kidney. This presentation was very similar to that observed in the HO-1 null mutant mice. In normal gestation the HO-1 enzyme is seen at high levels in the neonatal and fetal rat lung and liver, compared to adults.[17]

A current study found that HO expression in human placenta and placental bed implies a role in regulation of trophoblast invasion and placental function.[18] Furthermore, the results suggested a role for CO in placental function, trophoblast invasion, and spiral artery transformation.[19]

D. The Effect of carbon monoxide in pregnancy

Cigarette smoking during pregnancy has been recognized for over three decades to be associated with reduced risks of PET.[20] This paradoxical effect of exposure to tobacco during pregnancy, where smoking reduces the incidence of PET, but increases the perinatal morbidity and mortality and results in a well recognized health hazard to both the mother and her newborn, has long puzzled investigators.[21] A recent systematic review of the existing evidence found that the risk of PET in pregnant women who smoked was 32% lower than that among nonsmoking pregnant women.[22] Furthermore, pooled data from cohort and case-control studies showed that this inverse association was dose-related and remarkably consistent across studies conducted in various populations and countries.[23] A current study that measured urinary cotinine in order to assess tobacco exposure confirmed the reduced risk of developing PET with cigarette smoking.[24] Using data from the Collaborative Perinatal Project, it was recently demonstrated that smoking is associated not only with a reduced risk of hypertension during pregnancy, but also with a protective effect that appeared to continue even after cessation of smoking.[25]

Despite the accumulating data suggesting an inverse association between cigarette smoking and the risk of PET, little light has so far been shed on the pathophysiology behind the apparent protective role of smoking. Smokers are exposed to high concentrations of CO which is a simple diatomic gas molecule that shares some of the physiochemical properties of nitric oxide ("NO"). CO, like NO, stimulates soluble guanylyl cyclase and thereby raises intracellular levels of cyclic guanosine monophosphate ("cGMP") in vascular smooth muscle to produce endothelium-dependent arterial relaxation.[26] It is now recognized that CO may play a key role in the regulation of placental hemodynamics.[27] Platelet aggregation may also be prevented by CO generation.

It has recently been suggested that PET may reflect a state of impaired NO synthesis due to failure of the vasodilatation and decreased vascular reactivity. The similarity in the mechanisms of action of NO and CO in endothelium-dependent arterial relaxation suggest that CO formation could also have a contributory role in the pathogenesis of PET.[28] This is supported by recent observations that HO, which catalyzes the degradation of heme to biliverdin and CO, is expressed more intensely in the placenta, umbilical cord, and myometrium of preeclamptic patients compared with normal pregnant patients.[29]

Although possible roles of CO in pregnancy have recently been recognized, all previous studies have been based on laboratory analysis of tissue samples. Thus, these methods are difficult to implement and are time consuming and discomforting to the pregnant patients. Prior to applicant's discovery disclosed herein, it is believed that nobody has ever attempted to look for clinical applications to determine the CO concentration measuring a pregnant patient's breath. Nor was it known or even recognized to be useful to examine whether breath CO or ETCOc measurements could be used as a diagnostic and predictive tool in pregnant women.

E. End-Tidal Concentration of Carbon Monoxide and Measurement Thereof

The concentration of CO in the end-tidal breath, i.e., the gas that is last expelled in each breath, is presumed to be at equilibrium with the concentration in the blood. This is because the end-tidal breath contains predominantly, if not exclusively, the gas expelled from the alveoli in the lungs, which gas was within the alveoli for a time generally sufficient to equilibrate with the blood.

End-tidal carbon monoxide ("ETCO") concentrations, sometimes referred to as alveolar concentrations, can be measured in a variety of ways. A preferred methodology is described in U.S. Pat. No. 5,293,875, the disclosure of which is incorporated herein by reference, in which a breath sample is continuously drawn from the patient's breath stream and directed to a fast-responding carbon dioxide ($CO_2$) sensor and a slower responding CO sensor. The signals from the $CO_2$ sensor, the CO sensor and a measurement of inhaled CO concentration are used to calculate the end-tidal CO concentration.

There are numerous other methods by which an end-tidal breath sample can be collected and analyzed for CO including the basic method of having the patient breathe through a tube connected to a three-way valve. During the first portion of the breath, which is non-alveolar, the valve is set so that the exhaled breath is directed to a chamber or discharged to the ambient environment. Towards the end of the exhalation, the valve can be manually switched so that the breath is directed into a sampling container or bag. The breath collected in the container can then be analyzed for the end-tidal CO concentration.

This basic method can be improved by automating the actuation of the three-way valve based upon a variety of signals including $CO_2$ concentration, chest-wall movement, exhaled breath volume (described in U.S. Pat. No. 3,622,278), exhaled breath temperature, or changes in exhaled breath temperature (described in U.S. Pat. No. 4,248,245).

An alternative-method to obtain an end-tidal sample is to place the end of a syringe into a patient's breath stream and manually pull the plunger of the syringe back during the final portion of the exhalation phase so that an end-tidal sample is drawn into the syringe. This method can be improved by automating the movement of the syringe plunger using a variety of control signals including exhaled $CO_2$ concentration, chest-wall movement, exhaled breath volume or exhaled breath temperature (described in U.S. Pat. No. 4,220,162).

Still another way to obtain an end-tidal breath sample is to have the patient exhale through a reservoir which is much smaller than the tidal volume of the breath and has both inlet and outlet ports. The first portion of the breath is discharged to the ambient environment, while the end-tidal portion is trapped in the reservoir by either one-way check valves (described in U.S. Pat. No. 3,858,573), or by manually sealing the ports of the reservoir (described in U.S. Pat. No. 5,211,181).

OBJECTS AND SUMMARY OF THE INVENTION

The present invention relates to a method for using breath CO or ETCOc measurements to detect various pathological conditions in pregnant women including PIH, PET, PMC, and IUGR. The invention has further applications in the estimation of the severity of these abnormal conditions of pregnancy and in monitoring the response of such conditions to treatment.

The present invention provides a method for early detection of pathological conditions in pregnancy by measuring breath CO or ETCOc and can be applied in a hospital, clinic, or physician's office. The method can utilize a device such the Natus® CO-Stat® End Tidal Breath Analyzer (Natus Medical Inc., San Carlos, Calif.) to perform non-invasive, simple and rapid, automatic sampling and analysis of end expiratory air without the requirement for laboratory analysis or highly trained personnel. Thus, the device and method are capable of providing on-the-spot instant results vital for rapid treatment of such serious conditions of pregnancy.

Two separate studies were conducted. In the first study, ETCOc measurements were prospectively performed on three study groups of women in three separate medical centers (the "PIH/PET study"). The study groups included 52 women with PIH or symptoms of PET classified according to the American College of Obstetrics and Gynecology criteria (the "PIH/PET test group").[30] The control groups included 42 first and 63 third trimester normotensive pregnant women and 46 non-pregnant women.

In the second study, ETCOc measurements were made in 55 nonsmoking, healthy pregnant women (the "PMC study"). The study group included 10 women with PMC during the second half of their pregnancy (the "PMC group"), 13 women in active labor at term and 32 pregnant mothers at matched gestational ages not experiencing uterine contractions.

It is an object of the present invention to utilize breath CO or ETCOc measurements to identify, either directly or indirectly, fundamental disturbances in normal regulation of placental and myometrial function, thereby allowing both prediction and early detection of various severe disorders of normal physiology associated with the major morbidities of pregnancy. Particularly, the method would allow detection of pregnant patients at risk for PIH, PET, the HELLP Syndrome, PMC, and IUGR.

Another object of the present invention is to allow early detection of these various pregnancy related conditions utilizing a safe, inexpensive, non-invasive diagnostic tool which can be operated with little training in a plethora of locations which are easily accessible to regnant women. Moreover, obtaining breath CO or ETCOc measurements advantageously avoids the hazards associated with the handling of blood samples.

Further objects and advantages afforded by the present invention will be apparent from the detailed description hereinbelow.

BRIEF DESCRIPTION OF THE DRAWINGS

The appended drawings are presented to further describe the present invention and to assist in its understanding through clarification of its various aspects. The above discussion as well as other objects and advantages of the invention will be apparent to a person of ordinary skill in the art upon consideration of the following detailed description, taken in conjunction with the accompanying drawings, in which:

FIG. 1 illustrates, in connection with the PIH/PET study, a table charting the ETCOc concentrations for PIH/PET test group compared with a first and third trimester control group and a non-pregnant control group, including the mean, median and range for the four groups;

FIG. 2 illustrates, in connection with the PIH/PET study, a table charting the mean ETCOc concentrations for the PIH/PET test group compared with the third trimester control group for all three test locations;

FIG. 4 illustrates, in connection with the PIH/PET study, a table charting the percentages of pregnant women in the four test groups whose ETCOc concentrations were less than 1.2, 1.4 and 1.6 parts per million;

FIG. 5 illustrates, in connection with the PIH/PET study, a table charting the mean and range of gestational ages for the PIH/PET test group and the third trimester control group;

FIG. 8 illustrates, in connection with the PMC study, a table charting the mean and median maternal age, gravidity and parity for the study group and the control group;

FIG. 9 illustrates, in connection with the PMC study, a table charting the mean and range gestational age for the PMC group, the term labor group, and the no-contraction-at-term group;

FIG. 10 illustrates, in connection with the PMC study, a table charting the mean, median and range of ETCOc concentrations for the study group and the control group;

FIG. 11 illustrates, in connection with the PMC study, a table charting the mean, median and range of ETCOc concentrations for the PMC group and the term labor group;

FIG. 12 illustrates, in connection with the PMC study, a table charting the mean, median and range of ETCOc concentration for the PMC group, the term labor group, and the control group;

FIG. 14 illustrates, in connection with the PMC study, a table charting the percentages of pregnant women in the study group and the control group whose ETCOc concentrations were less than 1.2, 1.3 and 1.6 parts per million;

FIG. 16 illustrates, in connection with the PMC study, a table charting the percentages of pregnant women in the PMC group and the term labor group whose ETCOc concentrations were less than 1.2, 1.3 and 1.6 parts per million.

DETAILED DESCRIPTION OF THE INVENTION

I. Breath Carbon Monoxide Levels are Lower in Women with Pregnancy-Induced Hypertension and Preeclampsia A. Discussion of Test Protocol and Test Results Breath CO measurements were prospectively performed in three tertiary medical centers (Stanford Medical Center, Stanford, Calif.; Case Western Reserve, Cleveland, Ohio and Sheba Medical Center, Tel-Hashomer, Israel) on three study groups of women. The study group included 52 women with PIH or symptoms of PET classified according to the American College of Obstetrics and Gynecology criteria.[31] The control groups included 42 first and 63 third trimester normotensive pregnant women and 46 non-pregnant women.

Exclusion criteria included smoking or passive smoking (defined as living with a household member who smoked or presence in a room where smoking was allowed during the previous 24 hours), respiratory illness, clinical signs of hemolysis (defined as LDH levels over 400 IU/L) or HELLP syndrome, exposure to a known hemolytic agent, fever or evidence of an infectious disease, and any other significant medical illness such as diabetes mellitus. All women gave informed consent for their participation in accordance with the institution's human investigation review board approval of the study protocol.

ETCOc measurements were obtained using a portable automated CO analyzer (Natus® CO-Stat® End Tidal Breath Analyzer, Natus Medical Inc., San Carlos, Calif.).[32] Each mother gave an expiratory sample, following instruction by one of the investigators. Samples were collected and simultaneously analyzed by obtaining breath exhaled from women, resting for at least 15 minutes, via a 5F catheter placed 2 cm into the anterior nares.

Figure 3:
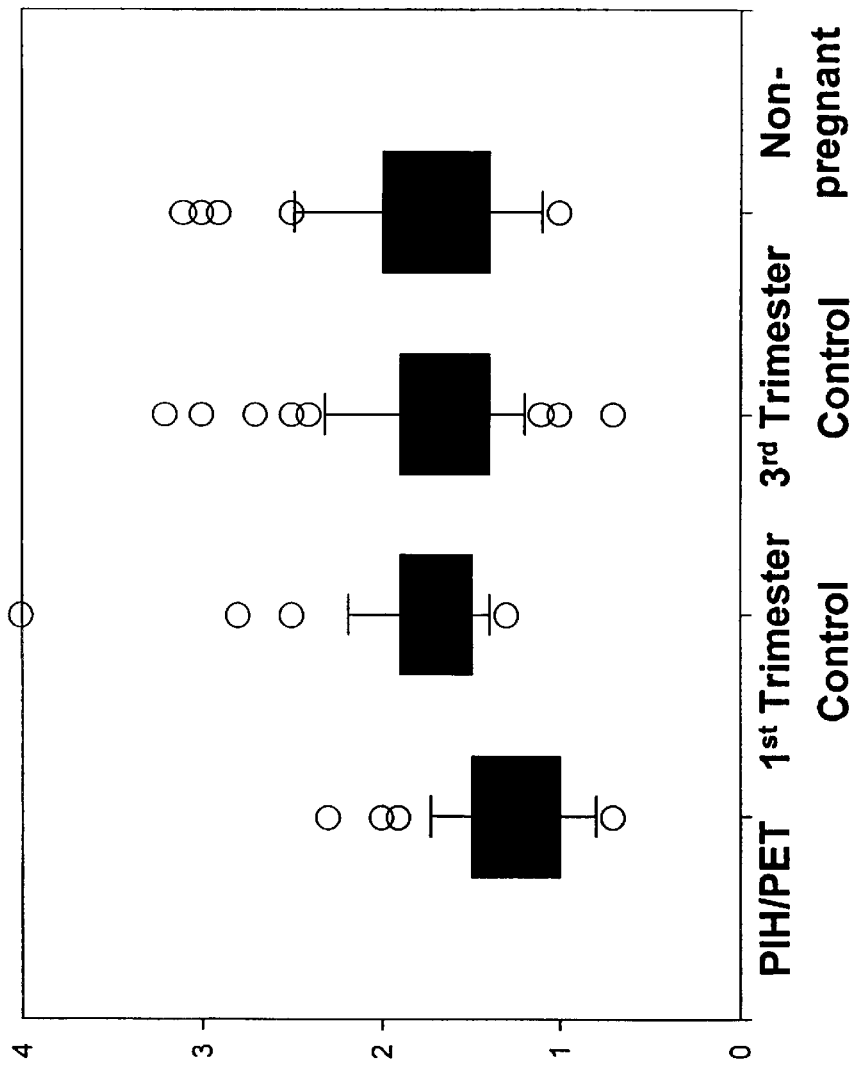
FIG. 3 illustrates, in connection with the PIH/PET study, a graphical representation of the mean, median and range of the ETCOc concentrations for the PIH/PET test group, the first and third trimester control groups, and the non-pregnant control group.

The study and control groups were similar in respect to maternal age, gravidity, parity, body weight and body mass. The test data demonstrates that patients in the PIH/PET test group have a statistically significantly lower (p<0.0001) mean level of ETCOc compared with the women in the first and third trimester normotensive pregnant and non-pregnant control groups (1.29±0.35 vs. 1.72±0.46, and 1.72±0.54 ppm respectively) (FIG. 1). Additionally, in all three test centers, the ETCOc levels were significantly lower between the PIH/PET patient group and the control groups despite widely differing patient populations (FIG. 2). The test data also demonstrated that the range of distribution of the ETCOc measurements in the PIH/PET control group patients were strikingly lower than in the control groups (FIG. 3).

When a statistical cut-off level of 1.6 parts-per-million ETCOc concentration is examined, the ETCOc measurements of almost 90% of the PIH/PET test group patients fall below this level, as compared to less than 50% of the patients in the control groups (FIG. 4). When a cut-off level of 1.2 parts-per-million ETCOc concentration is examined, almost half of the patients in the PIH/PET group have ETCOc concentrations which fall below this level, as opposed to less than 10% of the control groups (FIG. 4).

Figure 6:
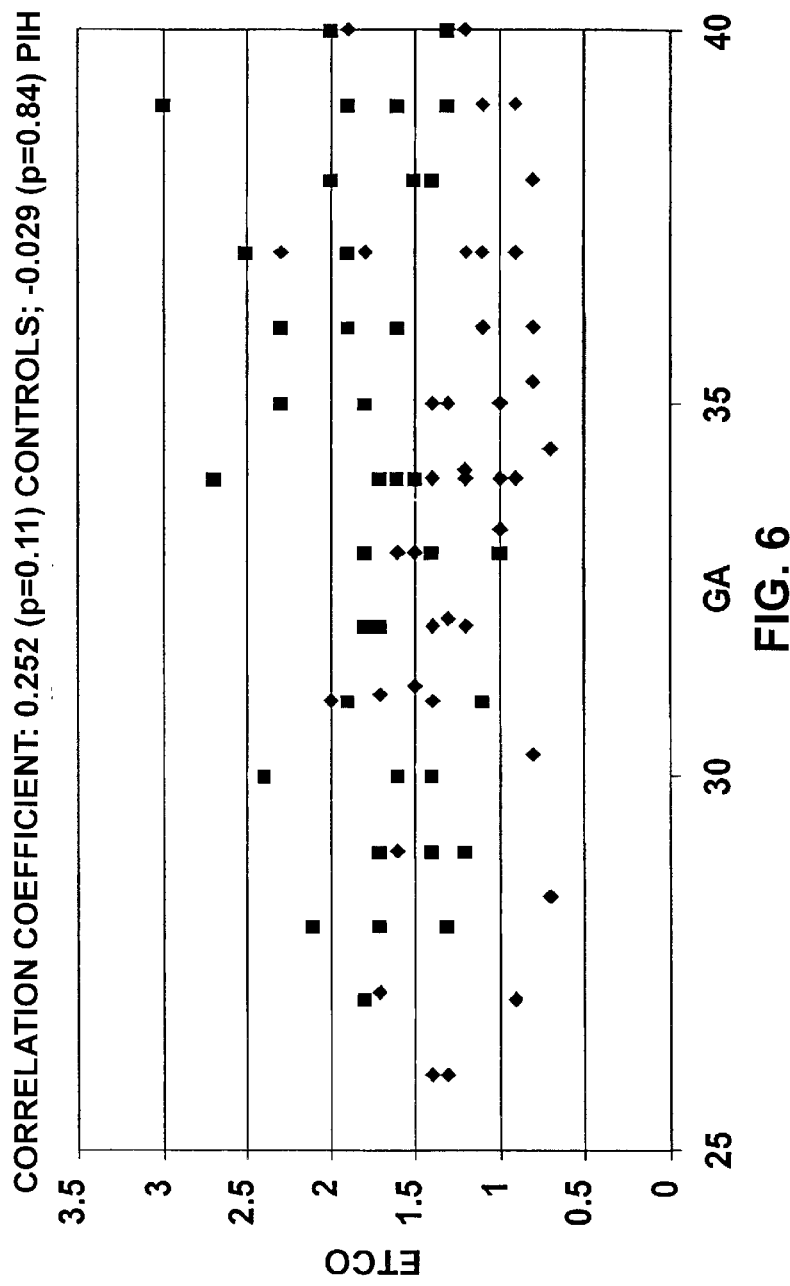
FIG. 6 illustrates, in connection with the PIH/PET study, a graphical representation of the ETCOc concentration by gestational age (in weeks) during the third trimester of pregnancy.
Figure 7:
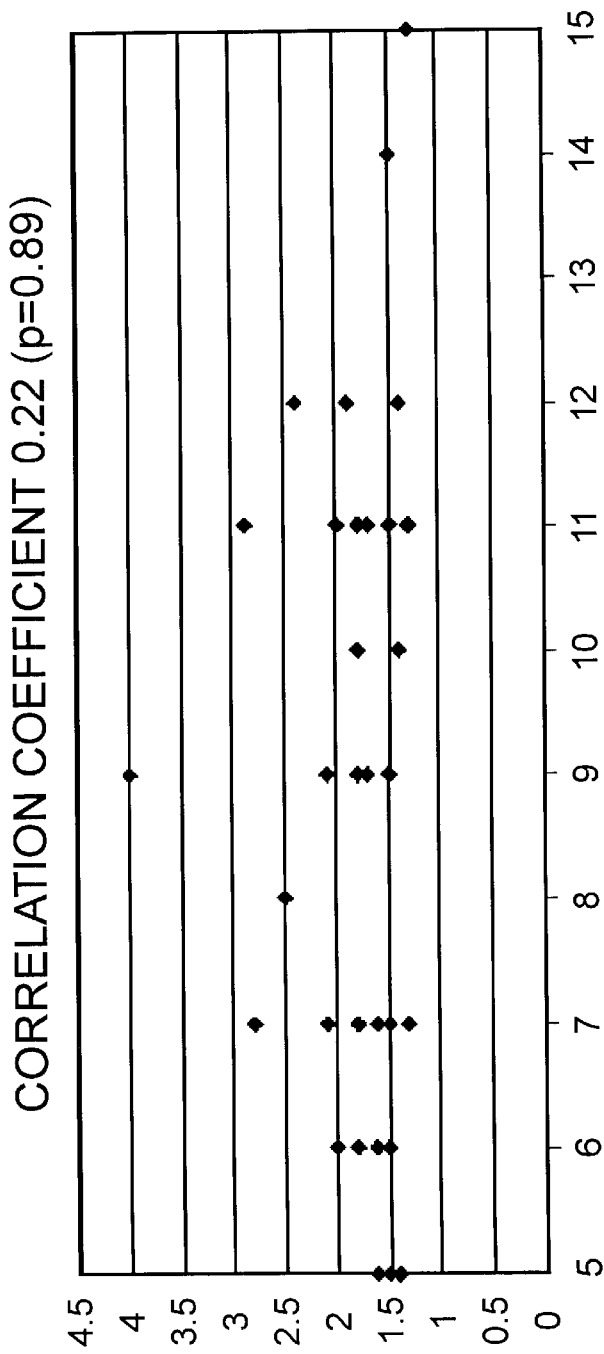
FIG. 7 illustrates, in connection with the PIH/PET study, a graphical representation of the ETCOc concentration by gestational age (in weeks) during the first trimester of pregnancy.

Since the gestational age was similar in the study and third trimester control groups, the significant differences in ETCOc levels can not be attributed to the confounding effect of gestational age (FIG. 5). An analysis of the data clearly shows that the ETCOc levels were not significantly correlated with gestational age in the third trimester of pregnancy (FIG. 6). The same lack of correlation is found with regard to the first trimester data (FIG. 7).

It was therefore concluded that breath CO and ETCOc levels are actually significantly lower in women with PIH/PET. This finding was consistently observed in all three medical centers based on test groups encompassing widely differing patient populations. Furthermore, the data indicates that there are actual statistical values which can be calculated and tabulated as references (i.e., threshold values which can be used for comparative purposes to measurements from patients with unknown PIH/PET) which will represent the likelihood of onset or actual onset of PIH/PET.

Further investigation is required to determine if the lower CO levels reflect a deficient compensatory response to the increase in blood pressure or whether these are primary changes of significance to the understanding of the obscure pathogenesis of this common and severe disorder of pregnancy.

Additionally, it should be understood by a person of ordinary skill in the art that one can measure the breath CO and ETCOc values of healthy non-pregnant and healthy pregnant women, and empirically determine from a statistically reliable sample set—a reference set of values indicative of good health for the condition of interest. Then, the measured breath CO or ETCOc values of women whose health is unknown with respect to the condition that a person is attempting to detect, can be compared to this threshold to make a determination of whether or not the woman has the particular condition. In this way, a person of ordinary skill in the art can determine the "known" values for implementing the present invention.

B. Link Between Maternal Smoking and Reduced Incidence of Preeclampsia

The paradoxical effect of exposure to tobacco during pregnancy, where smoking reduces the incidence of PET, but increases the perinatal morbidity and mortality, has long puzzled investigators. CO has been implicated as responsible for some of the detrimental effects of smoking. This may be, at least in part, attributed to the high affinity of CO to fetal hemoglobin. Maternal CO levels in the exhaled air were shown to be associated with a linear decrease in birth weight.[33] However, the physiological role of CO has only recently been recognized. It is now known that CO can act as an endogenous vasodilator.[34] It was therefore suggested that the heme degradation pathway and CO formation could have a contributory role in the regulation of placental hemodynamics.[35] Furthermore, a close relationship was found in animal models between heme metabolism and blood pressure regulation.[36] Thus, the inventor proposed that in pregnancy CO, generated by smoking, may have, in addition to its familiar adverse effect, a direct influence on the fetal-placental vascularture, resulting in the so-called "protective" effect against PET.

The results of this study, showing a significantly lower level of CO in women with PET, support the concept that moderately elevated levels of CO likely offer an advantage in terms of the risk for PET.

Increased breath CO or ETCOc measurements can reflect exposure to both exogenous and endogenous sources of CO. Smoking is the most important environmental source of CO. Measurement of CO levels in the maternal breath has been shown in late pregnancy to accurately assess the exposure of women to tobacco smoke.[37] The major endogenous source of CO is due to increased CO production when hemolysis occurs, because hemoglobin degradation is the only metabolic pathway which produces significant amounts of this gas.[38]

Little is known about the physiologic role of CO in pregnancy. However, accumulating evidence implies that a reduction in the synthesis of NO may contribute to the pathogenesis of hypertension in pregnancy.[39] Since the similarity in the mechanisms of action of NO and CO in endothelium dependent arterial relaxation is now realized, CO generated by smoke may influence the pathogenesis of PET. It is believed that CO may at least in part explain the lower incidence of PET among women who smoke.

C. Physiologic Role of CO in Preeclampsia

CO may act as an endogenous vasodilator[40] and can inhibit platelet aggregation.[41] It may therefore influence the regulation of uterine and feto-placental hemodynamics in normal pregnancy, and increased generation of CO in PET may serve as a compensatory response. This is consistent with a close relationship found in animal models between heme metabolism and blood pressure regulation.[42] In addition, it has been proposed that the poorly perfused fetoplacental unit in preeclamptic patients is the origin of oxygen free radicals and lipid peroxides.[43]

D. Relationship of Test Results for Prediction of HELLP Syndrome

The major endogenous source of CO is due to increased CO production when hemolysis occurs, because hemoglobin degradation is the only metabolic pathway which produces significant amounts of this gas.[44] Breath CO and ETCOc were accordingly shown to accurately identify hemolysis.[45] This is of significance since hemolysis, the hallmark of the HELLP Syndrome, is often difficult to identify early in women at risk for the HELLP Syndrome, as severe hypertension is not a constant or even a frequent finding in the HELLP Syndrome. Since the test results have demonstrated that breath CO and ETCOc levels measured during pregnancy are low in PET, it is believed that as the disease becomes more severe and deteriorates towards full-blown HELLP Syndrome, maternal hemolysis associated with HELLP Syndrome results in rising breath CO and ETCOc levels. Therefore, breath CO and ETCOc measurements provide an accurate means for very early recognition of the maternal hemolysis associated with the HELLP Syndrome. This would allow for delivery from the mother before severe morbidity results.

II. Breath Carbon Monoxide Levels are Lower in Women who Experience Premature Uterine Contractions The inventor proposed that breath CO measurements would be helpful in detecting women at risk of developing premature labor, thereby allowing early initiation of preventive treatment. Even if CO does not serve as the major endogenous inhibitor of myometrial contractility during pregnancy, very early changes in the quiescent state of the uterus during pregnancy may offset alterations in the HO—CO-cGMP pathway.

ETCOc measurements were prospectively performed using the aforementioned Natus® CO-Stat® End Tidal Breath Analyzer. Each mother gave an expiratory sample, following instruction by one of the investigators. Samples were collected and simultaneously analyzed by obtaining breath exhaled from women, resting for at least 15 minutes, via a 5F catheter placed 2 cm into the anterior nares.

Measurements were made in 55 nonsmoking, healthy pregnant women; 10 women with PMC during the second half of their pregnancy, 13 women in active labor at term and 32 pregnant mothers at matched gestational ages not experiencing uterine contractions.

Figure 13:
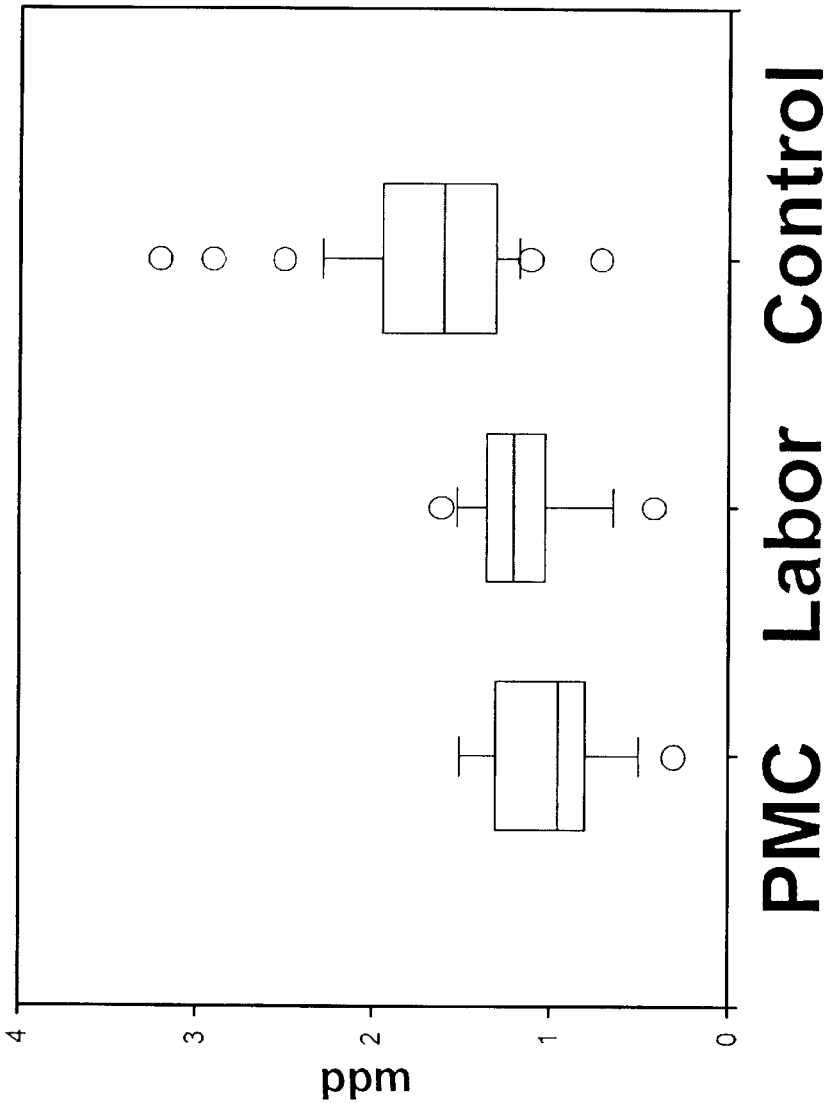
FIG. 13 illustrates, in connection with the PMC study, a graphical representation of the mean, median and range of ETCOc concentrations for the PMC group, the term labor group and the control group.

The women in the study group who had experienced uterine contractions had statistically similar maternal ages, gravidity and parity with those women who had not experienced uterine contraction (FIG. 8). As expected, the women who experienced PMC had a lower gestational age than the study and control term groups (FIG. 9). The mean ETCOc levels were statistically significantly lower ($p<0.001$) in women with PMC and in women actively delivering at term compared with women with no uterine contractions (FIG. 10). The ETCOc levels were also similar with regard to women experiencing pre-term and term uterine contractions (FIG. 11). The ETCOc levels were significantly lower in both women with PMC and active term labor compared with the control women with no uterine contractions (FIG. 12). The distribution of the ETCOc measurements clearly show lower levels and a lesser range of measurements in women with uterine contractions compared with the control group and with those women experiencing no uterine contractions (FIG. 13).

Figure 15:
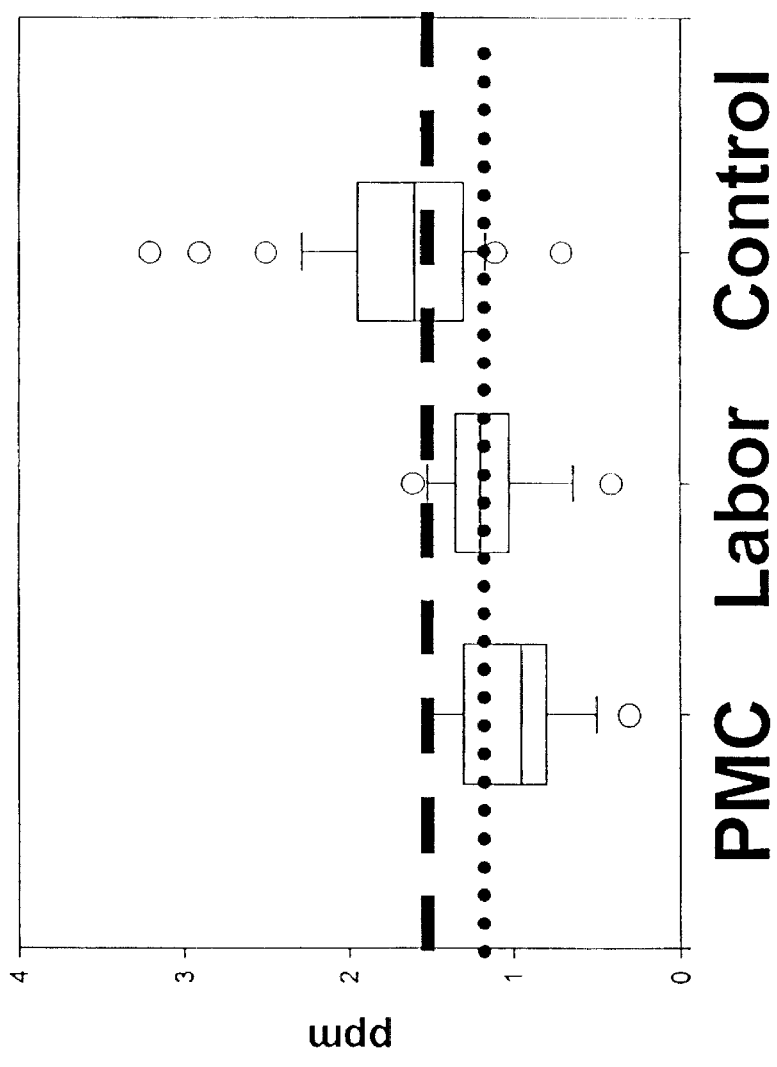
FIG. 15 illustrates, in connection with the PMC study, a graphical representation of the mean, median and range of ETCOc concentrations for the PMC group, the term labor groups and the control group.

When a statistical cut-off level of 1.6 parts-per-million ETCOc concentration is examined, the ETCOc measurements identified almost 96% of the women with uterine contractions as opposed to less than 40% of the women with no uterine contractions (FIG. 14). When a cut-off level of 1.2 parts-per-million ETCOc concentration is examined, the ETCOc measurements identified almost 50% of the women with uterine contractions as opposed to less than 10% of the women with no uterine contractions (FIG. 14). When the data is graphically presented, this correlation is even more clearly demonstrated (FIG. 15). Furthermore, while women with uterine contractions had a similar proportion of ETCOc measurements below 1.6 parts-per-million, women with PMC had significantly more measurements below 1.2 parts-per-million compared with women in active labor at term (FIG. 16).

It was therefore concluded that the ETCOc levels, and thus breath CO levels, were significantly higher in pregnant women with a relaxed myometrium and ETCOc levels, and thus breath CO levels, were significantly low in women with premature uterine contraction and active labor. Measurement of breath CO and ETCOc is therefore of considerable value in the clinical assessment of PMC. Furthermore, the data indicate that there are actual statistical values which can be calculated and tabulated as references which will represent the likelihood of onset or actual onset of premature uterine contractions.

III. End Tidal Carbon Monoxide Levels are Helpful in Detecting Women at Risk of Developing Intrauterine Growth Retardation In light of various recent observations, it is also believed that CO formation could have a contributory role in the pathogenesis of IUGR. Preliminary breath CO or ETCOc measurements in pregnant women with suspected IUGR fetuses suggest that such measurements can be helpful in detecting women at risk of developing IUGR, thereby allowing early initiation of follow-up and treatment of this pathology.

One skilled in the art will appreciated that the foregoing embodiments are presented for purposes of illustration and not of limitation.

I claim:

1. A method of detecting an increased risk of developing pregnancy-induced hypertension in a pregnant woman comprising the steps of:
   (a) collecting a breath sample from a pregnant woman;
   (b) measuring the carbon monoxide concentration in said breath sample;
   (c) comparing said measured concentration to a reference carbon monoxide concentration indicative of pregnancy-induced hypertension; and
   (d) determining that there is an increased risk of pregnancy-induced hypertension in response to said measured breath sample being lower than said reference concentration.

2. The method of claim 1 wherein said measured carbon monoxide concentration is an end-tidal carbon monoxide concentration.

3. The method of claim 1 wherein the collecting step further comprises continuously drawing said sample from said pregnant woman's breath stream; and determining the carbon monoxide concentration from said continuously drawn stream.

4. The method of claim 1 further comprising the step of measuring the breath carbon monoxide value of a sample set of women known not to suffer from pregnancy-induced hypertension; and determining from said sample set reference carbon monoxide values indicative of a lack of pregnancy-induced hypertension.

5. A method of detecting an increased risk of developing preeclampsia in a pregnant woman comprising the steps of:
 (a) collecting a breath sample from a pregnant woman;
 (b) measuring the carbon monoxide concentration in said breath sample;
 (c) comparing said measured concentration to a reference carbon monoxide concentration indicative of preeclampsia; and
 (d) determining that there is an increased risk of preeclampsia in response to said measured breath sample being lower than said reference concentration.

6. The method of claim 5 wherein said measured carbon monoxide concentration is an end-tidal carbon monoxide concentration.

7. The method of claim 5 wherein the collecting step further comprises continuously drawing said sample from said pregnant woman's breath stream; and determining the carbon monoxide concentration from said continuously drawn stream.

8. The method of claim 5 further comprising the step of measuring the breath carbon monoxide value of a sample set of women known not to suffer from preeclampsia; and determining from said sample set reference carbon monoxide values indicative of a lack of preeclampsia.

9. A method of detecting an increased risk of developing the HELLP Syndrome in a pregnant woman comprising the steps of:
 (a) collecting a breath sample from a pregnant woman;
 (b) measuring the carbon monoxide concentration in said breath sample;
 (c) comparing said measured concentration to a reference carbon monoxide concentration indicative of the HELLP Syndrome; and
 (d) determining that there is an increased risk of the HELLP Syndrome in response to said measured breath sample being greater than said reference concentration.

10. The method of claim 9 wherein said measured carbon monoxide concentration is an end-tidal carbon monoxide concentration.

11. The method of claim 9 wherein the collecting step further comprises continuously drawing said sample from said pregnant woman's breath stream; and determining the carbon monoxide concentration from said continuously drawn stream.

12. The method of claim 9 further comprising the step of measuring the breath carbon monoxide value of a sample set of women known not to suffer from the HELLP Syndrome; and determining from said sample set reference carbon monoxide values indicative of a lack of pregnancy-induced hypertension.

13. A method of detecting an increased risk of developing intrauterine growth restriction in a pregnant woman comprising the steps of:
 (a) collecting a breath sample from a pregnant woman;
 (b) measuring the carbon monoxide concentration in said breath sample;
 (c) comparing said measured concentration to a reference carbon monoxide concentration indicative of intrauterine growth restriction; and
 (d) determining that there is an increased risk of intrauterine growth restriction in response to said measured breath sample being lower than said reference concentration.

14. The method of claim 13 wherein said measured carbon monoxide concentration is an end-tidal carbon monoxide concentration.

15. The method of claim 13 wherein the collecting step further comprises continuously drawing said sample from said pregnant woman's breath stream; and determining the carbon monoxide concentration from said continuously drawn stream.

16. The method of claim 13 further comprising the step of measuring the breath carbon monoxide value of a sample set of women known not to suffer from intrauterine growth restriction; and determining from said sample set reference carbon monoxide values indicative of a lack of intrauterine growth restriction.

17. A method of detecting an increased risk of developing an actively laboring myometrium in a pregnant woman comprising the steps of:
 (a) collecting a breath sample from a pregnant woman;
 (b) measuring the carbon monoxide concentration in said breath sample;
 (c) comparing said measured concentration to a reference carbon monoxide concentration indicative of an actively laboring myometrium; and
 (d) determining that there is an increased risk of an actively laboring myometrium in response to said measured breath sample being lower than said reference concentration.

18. The method of claim 17 wherein said measured carbon monoxide concentration is an end-tidal carbon monoxide concentration.

19. The method of claim 17 wherein the collecting step further comprises continuously drawing said sample from said pregnant woman's breath stream; and determining the carbon monoxide concentration from said continuously drawn stream.

20. The method of claim 17 further comprising the step of measuring the breath carbon monoxide value of a sample set of women known not to suffer from an actively laboring myometrium; and determining from said sample set reference carbon monoxide values indicative of a lack of an actively laboring myometrium.

21. A method of detecting an increased risk of developing premature uterine contractions in a pregnant woman comprising the steps of:
 (a) collecting a breath sample from a pregnant woman;
 (b) measuring the carbon monoxide concentration in said breath sample;
 (c) comparing said measured concentration to a reference carbon monoxide concentration indicative of premature uterine contractions; and
 (d) determining that there is an increased risk of premature uterine contractions in response to said measured breath sample being lower than said reference concentration.

22. The method of claim 21 wherein said measured carbon monoxide concentration is an end-tidal carbon monoxide concentration.

23. The method of claim 21 wherein the collecting step further comprises continuously drawing said sample from said pregnant woman's breath stream; and determining the carbon monoxide concentration from said continuously drawn stream.

24. The method of claim 21 further comprising the step of measuring the breath carbon monoxide value of a sample set of women known not to suffer from premature uterine contractions; and determining from said sample set reference carbon monoxide values indicative of a lack of premature uterine contractions.

25. A method of detecting the onset of pregnancy-induced hypertension in a pregnant woman comprising the steps of:
  (a) collecting a breath sample from a pregnant woman;
  (b) measuring the carbon monoxide concentration in said breath sample;
  (c) comparing said measured concentration to a reference carbon monoxide concentration indicative of pregnancy-induced hypertension; and
  (d) determining that there is an increased risk of pregnancy-induced hypertension in response to said measured breath sample being lower than said reference concentration.

26. The method of claim 25 wherein said measured carbon monoxide concentration is an end-tidal carbon monoxide concentration.

27. The method of claim 25 wherein the collecting step further comprises continuously drawing said sample from said pregnant woman's breath stream; and determining the carbon monoxide concentration from said continuously drawn stream.

28. The method of claim 25 further comprising the step of measuring the breath carbon monoxide value of a sample set of women known not to suffer from pregnancy-induced hypertension; and determining from said sample set reference carbon monoxide values indicative of a lack of pregnancy-induced hypertension.

29. A method of detecting the onset of preeclampsia in a pregnant woman comprising the steps of:
  (a) collecting a breath sample from a pregnant woman;
  (b) measuring the carbon monoxide concentration in said breath sample;
  (c) comparing said measured concentration to a reference carbon monoxide concentration indicative of preeclampsia; and
  (d) determining that there is an increased risk of preeclampsia in response to said measured breath sample being lower than said reference concentration.

30. The method of claim 29 wherein said measured carbon monoxide concentration is an end-tidal carbon monoxide concentration.

31. The method of claim 29 wherein the collecting step further comprises continuously drawing said sample from said pregnant woman's breath stream; and determining the carbon monoxide concentration from said continuously drawn stream.

32. The method of claim 29 further comprising the step of measuring the breath carbon monoxide value of a sample set of women known not to suffer from preeclampsia; and determining from said sample set reference carbon monoxide values indicative of a lack of preeclampsia.

33. A method of detecting the onset of the HELLP Syndrome in a pregnant woman comprising the steps of:
  (a) collecting a breath sample from a pregnant woman;
  (b) measuring the carbon monoxide concentration in said breath sample;
  (c) comparing said measured concentration to a reference carbon monoxide concentration indicative of the HELLP Syndrome; and
  (d) determining that there is an increased risk of the HELLP Syndrome in response to said measured breath sample being greater than said reference concentration.

34. The method of claim 33 wherein said measured carbon monoxide concentration is an end-tidal carbon monoxide concentration.

35. The method of claim 33 wherein the collecting step further comprises continuously drawing said sample from said pregnant woman's breath stream; and determining the carbon monoxide concentration from said continuously drawn stream.

36. The method of claim 33 further comprising the step of measuring the breath carbon monoxide value of a sample set of women known not to suffer from the HELLP Syndrome; and determining from said sample set reference carbon monoxide values indicative of a lack of pregnancy-induced hypertension.

37. A method of detecting the onset of intrauterine growth restriction in a pregnant woman comprising the steps of:
  (a) collecting a breath sample from a pregnant woman;
  (b) measuring the carbon monoxide concentration in said breath sample;
  (c) comparing said measured concentration to a reference carbon monoxide concentration indicative of intrauterine growth restriction; and
  (d) determining that there is an increased risk of intrauterine growth restriction in response to said measured breath sample being lower than said reference concentration.

38. The method of claim 37 wherein said measured carbon monoxide concentration is an end-tidal carbon monoxide concentration.

39. The method of claim 37 wherein the collecting step further comprises continuously drawing said sample from said pregnant woman's breath stream; and determining the carbon monoxide concentration from said continuously drawn stream.

40. The method of claim 37 further comprising the step of measuring the breath carbon monoxide value of a sample set of women known not to suffer from intrauterine growth restriction; and determining from said sample set reference carbon monoxide values indicative of a lack of intrauterine growth restriction.

41. A method of detecting the onset of an actively laboring myometrium in a pregnant woman comprising the steps of:
  (a) collecting a breath sample from a pregnant woman;
  (b) measuring the carbon monoxide concentration in said breath sample;
  (c) comparing said measured concentration to a reference carbon monoxide concentration indicative of an actively laboring myometrium; and
  (d) determining that there is an increased risk of an actively laboring myometrium in response to said measured breath sample being lower than said reference concentration.

42. The method of claim 41 wherein said measured carbon monoxide concentration is an end-tidal carbon monoxide concentration.

43. The method of claim 41 wherein the collecting step further comprises continuously drawing said sample from said pregnant woman's breath stream; and determining the carbon monoxide concentration from said continuously drawn stream.

44. The method of claim 41 further comprising the step of measuring the breath carbon monoxide value of a sample set of women known not to suffer from an actively laboring myometrium; and determining from said sample set reference carbon monoxide values indicative of a lack of an actively laboring myometrium.

45. A method of detecting the onset of premature uterine contractions in a pregnant woman comprising the steps of:

(a) collecting a breath sample from a pregnant woman;
(b) measuring the carbon monoxide concentration in said breath sample;
(c) comparing said measured concentration to a reference carbon monoxide concentration indicative of premature uterine contractions; and
(d) determining that there is an increased risk of premature uterine contractions in response to said measured breath sample being lower than said reference concentration.

46. The method of claim 45 wherein said measured carbon monoxide concentration is an end-tidal carbon monoxide concentration.

47. The method of claim 45 wherein the collecting step further comprises continuously drawing said sample from said pregnant woman's breath stream; and determining the carbon monoxide concentration from said continuously drawn stream.

48. The method of claim 45 further comprising the step of measuring the breath carbon monoxide value of a sample set of women known not to suffer from premature uterine contractions; and determining from said sample set reference carbon monoxide values indicative of a lack of premature uterine contractions.

49. A method of assessing an increased risk of preeclampsia in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of preeclampsia; and
(d) determining that there is an increased risk of preeclampsia in response to said measured breath sample being lower than said reference concentration.

50. A method of assessing an increased risk of pregnancy-induced hypertension in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of pregnancy-induced hypertension; and
(d) determining that there is an increased risk of pregnancy-induced hypertension in response to said measured breath sample being lower than said reference concentration.

51. A method of assessing an increased risk of intrauterine growth restriction in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of intrauterine growth restriction; and
(d) determining that there is an increased risk of intrauterine growth restriction in response to said measured breath sample being lower than said reference concentration.

52. A method of assessing an increased risk of an actively relaxed myometrium in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of an actively relaxed myometrium; and
(d) determining that there is an increased risk of an actively relaxed myometrium in response to said measured breath sample being lower than said reference concentration.

53. A method of assessing an increased risk of the HELLP Syndrome in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of the HELLP Syndrome; and
(d) determining that there is an increased risk of the HELLP Syndrome in response to said measured breath sample being lower than said reference concentration.

54. A method of assessing an increased risk of premature uterine contractions in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of premature uterine contractions; and
(d) determining that there is an increased risk of premature uterine contractions in response to said measured breath sample being lower than said reference concentration.

55. A method of assessing an increased risk of fetal hypoxia in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of fetal hypoxia; and
(d) determining that there is an increased risk of fetal hypoxia in response to said measured breath sample being lower than said reference concentration.

56. A method of assessing an increased risk of placental abruption in smokers according to the exposure to active and passive smoke comprising:
(a) collecting a breath sample from a pregnant smoking woman;
(b) measuring the carbon monoxide concentration in said breath sample;
(c) comparing said measured concentration to a reference carbon monoxide concentration indicative of placental abruption; and
(d) determining that there is an increased risk of placental abruption in response to said measured breath sample being lower than said reference concentration.

\* \* \* \* \*